United States Patent [19]

Lin

[11] Patent Number: 5,835,384
[45] Date of Patent: Nov. 10, 1998

[54] INTER-LABORATORY PERFORMANCE MONITORING SYSTEM

[75] Inventor: Lawrence I-kuei Lin, Riverwoods, Ill.

[73] Assignee: Dade International Inc., Deerfield, Ill.

[21] Appl. No.: 661,208

[22] Filed: Jun. 10, 1996

Related U.S. Application Data

[62] Division of Ser. No. 272,239, Jul. 8, 1994, Pat. No. 5,532,941.

[51] Int. Cl.$^6$ .............................. G06F 15/16; G06G 7/48
[52] U.S. Cl. ........................ 364/552; 364/554; 364/550; 364/571.01; 364/138
[58] Field of Search .................................... 364/552, 554, 364/550, 571.01–571.08, 582, 138; 264/468

[56] References Cited

U.S. PATENT DOCUMENTS

| | | | |
|---|---|---|---|
| 4,399,502 | 8/1983 | Macdonald et al. | 364/189 |
| 4,858,154 | 8/1989 | Anderson et al. | 364/554 |
| 4,870,590 | 9/1989 | Kawata et al. | 364/468 |
| 5,257,212 | 10/1993 | Kildel-Brandt et al. | 364/582 |
| 5,351,202 | 9/1994 | Kurtzberg et al. | 364/552 |
| 5,440,478 | 8/1995 | Fisher et al. | 364/188 |

FOREIGN PATENT DOCUMENTS

| | | | |
|---|---|---|---|
| 9013794 | 11/1990 | WIPO | G01D 18/00 |

OTHER PUBLICATIONS

Chemometrics and Intelligent Laboratory System, 12:69–79, 1991; Danzer, et al; An Expert System for the Evaluation and Interpretation of Interlaboratory Comparisions.

Measurement Techniques, 35:684–687,; Pal'chick, et al.; Method for Processing the Data of Interlabororatory Comparisons, Jun. 1992.

Asaay Validation Using the Concordance Correlation Coefficient, by Lawrence I–Kuei Lin, Biometrics 48; pp. 599–604, Jun. 1992.

A Concordance Correlation Coefficient to Evaluate Reproducibilty, by Lawarance I–Kuei Lin, Biometrics 45, pp. 255–268, Mar. 1989.

*Primary Examiner*—Edward R. Cosimano
*Assistant Examiner*—Kamini S. Shah
*Attorney, Agent, or Firm*—Charles S. Oslakovic

[57] ABSTRACT

A system and method for producing quality control evaluation information for each instrument in a large group of instruments making up a peer group which periodically (such as daily) run a set of control samples from a common lot of control materials. The control data from all instruments is reported electronically to a central station which collects all of the data and stores it along with identification information. The central station selects a golden peer group of the instruments which meet certain minimum operating criteria, and determines control targets from the golden peer group using techniques which assure horizontal and vertical robustness, so as to eliminate the need for any manual editing of the control data. A concordance correlation coefficient is determined for each instrument against the control targets, with the CCC covering an interval (such as a month). The distribution of CCC's for all instruments in the peer group is determined, and each instrument is rated with respect to the distribution. The CCC evaluation is also used to select the golden peer group for the next interval.

13 Claims, 9 Drawing Sheets

INTER-LABORATORY PERFORMANCE MONITORING SYSTEM

This is a division of application Ser. No. 08/272,239, filed on Jul. 8, 1994 now U.S. Pat. No. 5,532,941.

FIELD OF THE INVENTION

This invention relates to the monitoring of widely dispersed instruments and in a particular embodiment to inter-laboratory quality control monitoring and reporting for validation of laboratory analyses.

BACKGROUND OF THE INVENTION

There are a number of applications in which a widely dispersed array of laboratory instruments, sometimes of different kinds, are used to perform the same quantitative tests on unknown materials. In theory, a given unknown sample should produce the same results when analyzed on any system. In order to keep such systems in calibration, they are typically operated to produce calibration control data periodically, such as once per day.

Quality monitoring systems have been available for collecting the control data (calibration data on identical control samples) from a large number of instruments, and processing it to rate the performance of each instrument with respect to the performance of the group as a whole. This procedure is employed to a large extent in laboratories which analyze test samples for medical purposes. Hospitals collect large quantities of samples of various types and direct them to the hospital laboratory where they are automatically analyzed in special purpose laboratory instruments. For example, such measurements are made on triglycerides, glucose, cholesterol, total protein, and liver enzymes, to name just a few. At least once per day, and sometimes once per shift, a set of known control samples taken from a lot obtained from a central standard agency, is processed in the instrument and a set of control data measurements obtained. Usually, the standards are at 2 or at 3 points, a typical example utilizing 3 points for low, medium and high values of, for example, triglycerides. The control readings are stored and later dispatched to an organization which collects like data from a large number (preferably all) laboratories making the same tests and using the same control materials. The data is then processed utilizing certain statistical techniques to determine performance ratings for the laboratories. Typically the data from all of the laboratories is averaged or otherwise combined to provide a peer group mean, and the control data from each of the laboratories is evaluated against the peer group mean to determine the performance for that laboratory. But, considering that there might be three control levels for each laboratory, and each period may encompass multiple days (or shifts) of operations, it is not a simple matter to provide an easily understandable and reliable rating to advise a laboratory of how it is performing with respect to its peers.

An additional problem with such techniques is the quality of the peer group readings are sometimes compromised by utilizing all of the control data from all of the participating laboratories in setting the standard for the peer group determination. As a result, the standard might be skewed by including a number of badly performing laboratories in setting it, and the standard deviation (SD) from the average may be widened, giving a false sense of "goodness" to a marginally performing laboratory.

Attempts are sometimes made to minimize the effect of outliers (data points significantly different than the majority of readings), particularly in the computation of target values for the peer group. However, this is typically attempted by manual editing of the data intended to identify and remove from consideration readings containing outliers. This not only introduces an aspect of subjective variability into the overall process, but also introduces an element of effort and further delay in the rating process.

In many cases, hospitals and laboratories will edit their data before transmitting it to the agency which produces the ratings, further compromising the integrity of the overall system. In some cases, certain hospitals will run a larger number of control samples than others, and the former group of hospitals will, in some systems, be rewarded with an undeserved weight being given to their control readings as opposed to those of hospitals which take fewer control readings.

A further shortcoming of rating systems used in the past is timeliness of reporting. The data collection and editing process can take an inordinate amount of time, particularly in view of the fact that at least some of the data which must be reported is reported manually, and most of the data requires manual editing (as pointed out above). The enormity of the quantity of data can be better appreciated when one recognizes that data is being collected and ratings made for literally dozens of tests, each defining its own peer group. The final ratings for any test cannot be determined until all of the data for that test is obtained and input. This typically results in a situation where ratings, when they are distributed to the laboratories being rated, are based on data which can be on the order of six weeks old. It would be useful for laboratories, particularly those performing medical tests, to have a more current indication of their performance with respect to their peers, so that if a laboratory is performing out of control, that fact can be brought to light at the earliest possible moment.

SUMMARY OF THE INVENTION

In view of the foregoing, it is a general aim of the present invention to provide a highly automated quality control system for instruments, in which peer group determinations are automatically made from data reported automatically, and in which the rating is made in a simple, readily understandable fashion indicative of both precision and accuracy.

In that respect, it is a detailed object of the present invention to use the concordance correlation coefficient (CCC) as a measure of instrument performance, the CCC serving to evaluate control readings from a given instrument against a golden peer group target determined from a subset of the good performing instruments within the larger group.

In accordance with the last aspect, it is an object to employ, as a golden peer group for producing target values, only the instruments within the peer group which are performing at an acceptable or otherwise predetermined level of quality. It is a feature of the invention that all of the instruments in the group are rated on the CCC and its relationship to the CCC distribution of all instruments in the peer group. A further feature then uses this CCC rating to select the subset of golden peer group instruments from the larger group for the next evaluation.

An object of the invention to provide for the automatic input of data from the geographically dispersed instruments, preferably by communication line, and to pass such data automatically to the storage area from which the peer group targets are determined without the need for manual editing. In that respect, an objective is to utilize automatic means for minimizing the effects of outliers on the peer group targets, but while allowing an instrument to be rated on its full set of data which includes the outliers.

A resulting object is to report quality ratings to the individual laboratories in a timely fashion, shortly after the end of the interval for which the rating is to be performed. It is a further object to allow the provision of a rating on demand based on the data at hand at that point.

It is a feature of the invention that the instruments produce control data at widely geographically dispersed locations, and the control data readings are input to the system from those widely dispersed geographic areas via a communications medium linking all of the instruments to a central station. The central station is made up of a number of modules, including a communication interface, and a data storage module for storing all of the control data received from the dispersed instruments, along with identifiers associating the source of the data with the data itself. A target module operates on the collected data at predetermined intervals, or on demand, and is adapted to establish control targets. The target module operates in conjunction with a status memory which identifies the good performing subset of instruments known as the golden peer group. The status memory assists in selecting from the control data storage module the data originating from the golden peer group laboratories. That data is processed to produce targets in the target module. Means are utilized for minimizing the effect of outliers; such means includes processing across time for each member of the peer group, to assure horizontal robustness. Preferably, the time-related processing utilizes a short period (such as a week) for finding a moving median, and utilizes for that instrument on any given day the median value from a week-long period including that day. Vertical robustness is enhanced by processing the data for a given day from all instruments in the golden peer group by an M-estimation technique. By these horizontal and vertical robustness measures, the effect of outliers is minimized, but importantly without the need to manually edit the data. The result of this procedure is the production of a set of target values (determined from the golden peer group) for each day of the period for which a quality control rating is to be provided.

A concordance correlation comparator then compares the targets (for each day) against the control readings for each instrument for each day over an interval, such as a month. In accordance with the invention, a concordance correlation coefficient is produced for each instrument for the interval. The concordance correlation coefficient rates both the accuracy and the precision of the instrument readings with respect to the golden peer group target reading for the interval in question, and provides a single number for the interval which measures accuracy and precision. It is also possible, according to a subsidiary feature of the invention, to rate the instrument against a fixed target (as opposed to the moving target day by day peer group described above). The fixed target is a cumulative average of the data taken from all of the golden peer group instruments from the beginning of the current lot of the control sample. That average is updated on a daily basis, to provide a fixed target. In a fashion similar to that described above, a concordance correlation coefficient is produced for each instrument for the interval in question against the fixed target. Both measures are preferably reported to the laboratory. The CCC for all instruments in the peer group are also combined to determine the CCC distribution for the entire peer group. Each instrument is rated with respect to this distribution. By virtue of the rapid processing, without the need for manual editing, and by virtue of the automatic selection of the golden peer group, and by virtue of the further requirement in the preferable systems that the only laboratories which will be selected for the golden peer group are those which report data automatically by communication (on a daily basis), once the period for which the rating to be performed is at an end, processing can begin immediately and reports distributed to each of the laboratories on the day after the close of the interval. It will thus be appreciated that the invention satisfies the need for timeliness in being able to report quality control ratings on a periodic basis in a very timely fashion. The concordance correlation coefficients for all of the instruments are continually monitored. In addition to reporting of results to the laboratories, those instruments which exhibit "good" performance over a recent historical period (such as 3 months) are identified in a status memory. These instruments are then selected as the golden peer group for the next succeeding period. As a result, those instruments operating out of acceptable standards will be eliminated from the peer group target computations so as not to compromise the targets, and provide a better and more precise rating of the actual performance of each instrument.

In accordance with the timeliness aspect of the invention, while it may be desirable to operate the quality control system to produce reports on a monthly basis, by virtue of the automatic communication, elimination of the need for manual editing, and the ready availability of the data, the peer group identification, and the like, a rating can be determined on demand at any point during the period. Thus, for example, should a government regulator decide that today is the day he needs a rating for all instruments within the system, the rating can be generated without undue burden. If a laboratory is concerned about the performance of an instrument with respect to the peer group, the performance of that instrument can be determined against the entire peer group, and without affecting the data bases or the normal periodic generation of quality control information. Indeed, in a currently preferred system, in addition to maintaining a monthly record of ratings, a CCC evaluation is performed on a daily basis, and a "current" window is updated on a daily basis. For example, the current window can comprise the most recent 50 days, and it can be updated on a daily basis, with daily reports issuing to the laboratories. At the end of a month, in addition to updating the current window, the monthly comparison is also performed, and that data is recorded for historical purposes.

Other objects and advantages will become apparent from the following detailed description when taken in conjunction with the drawings, in which:

DETAILED DESCRIPTION OF THE PREFERRED EMBODIMENTS

While the invention will be described in connection with certain preferred embodiments, there is no intent to limit it to those embodiments. On the contrary, the intent is to cover all alternatives, modifications and equivalents included within the spirit and scope of the invention as defined by the appended claims.

Figure 1:
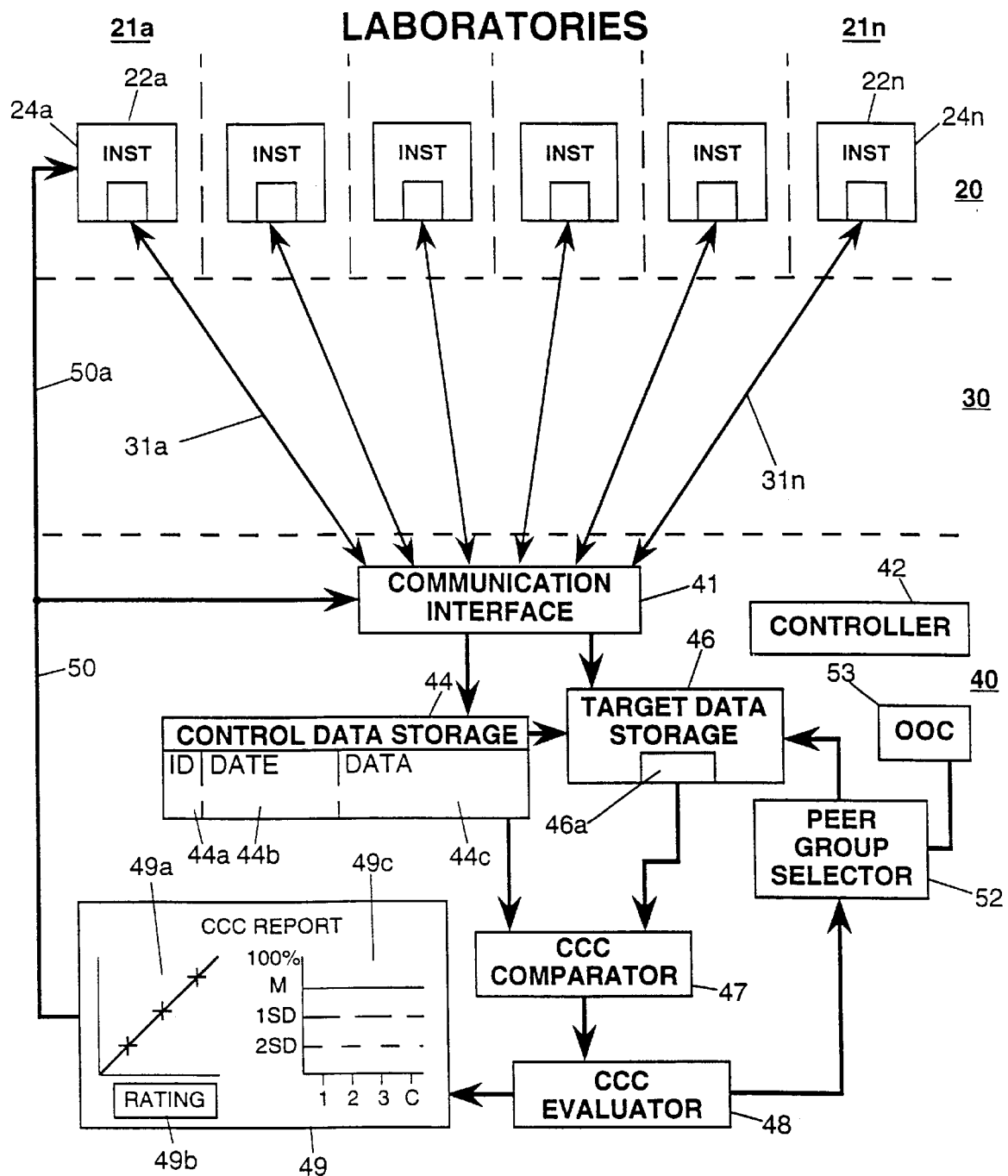
FIG. 1 is a block diagram illustrating, at a global level, a quality control system exemplifying the present invention.

Turning now to the drawings, FIG. 1 schematically illustrates a quality control system exemplifying the present invention. The reference numerals 20, 30 and 40 are utilized to distinguish three geographically distinct areas utilized by the invention. The area 20 comprises a plurality of geographically distributed laboratories 21a–21n. The laboratories may be distributed across the country or across the world. Each laboratory has at least one instrument 22a–22n of the type to be monitored in a quality control system according to the present invention. Each laboratory, or each instrument 22a–22n has a data storage and communication module 24a–24n for capturing control data and reporting such control data to the quality control monitoring station.

The second area 30 of the system comprises a communication network for communicating between the laboratory sites 20 and a central quality control site 40. The communication network 30 preferably includes links established on the public telephone system as by dialing up through the normal commercially available telecommunication channels. For closely located laboratories or for laboratories where there is a high concentration of communication, leased lines can be provided. The connections 31a–31n represent bi-directional communication links, typically the conventional telephone connection, between the laboratory sites 20 and the central station 40. The importance of the electronic communication interface between the geographically dispersed laboratories 20 and the central station 40 will become apparent when one appreciates the quantity of data which must be funneled into, sorted, stored and processed at the central station before any peer group evaluation can be made. Those skilled in the art will thus appreciate that electronic communication and automatic processing are integral features of a practical system constructed to practice the present invention.

In practicing the invention, a central station is connected to the laboratory sites 20 via the communication network 30, and includes means for accepting control data from the laboratory sites and automatically processing it to select a golden peer group, derive target data from that group, to compare the performance of each laboratory against those targets, and to provide a single statistic for a given period to rate each laboratory with respect to all its peers.

Before proceeding with the detailed description, certain definitional issues should be considered. The words "laboratory" and "instrument" are used somewhat interchangeably in this specification. However, it will be clear to those skilled in the art, particularly in the medical application, that a laboratory will have many instruments performing different types of tests. Insofar as application of the invention is concerned, each of those instruments can be rated with respect to its peers, and thus a given laboratory will be a member of a number of peer groups, typically one for each of its instruments. Thus, it is most technically accurate to refer to instruments and control data from instruments and distribution of CCC's for instruments; however, laboratory will occasionally be referred to, herein, realizing that comparisons and ratings are not done laboratory-wide, but on an instrument-by-instrument basis.

Also on the matter of definition, the concepts of a peer group and a golden peer group will be outlined. A peer group is considered to be those instruments using the same lot of control material at about the same time. Thus, the peer group in the language employed thus far is considered to be the entire group of instruments (running the same test with the same control materials at the same time). The golden peer group, on the other hand, is a subset of the peer group. As will be explained in greater detail below, the golden peer group is selected from the peer group as being those instruments which are performing at a predetermined level of operation. In the presently preferred practice of the invention, that level is determined to be within one standard deviation of the mean of all instruments, rated on the basis of the CCC determined for all instruments against the golden peer group. The instruments which meet the one SD limitation for three successive months are selected as members of the golden peer group, and the golden peer group is utilized to set the targets. Each instrument is then evaluated against the thus-set targets to determine its CCC, and the CCC's for all instruments are then combined to determine the norm and the standard deviation from the norm, and the results (both the numerical CCC results and the position of that instrument's CCC with respect to all of its peers) are reported to each individual laboratory.

With respect to time intervals, as a generality, in the medical application it will be typical to report control data on a daily basis and to accumulate such data for statistical reporting for a longer interval, such as monthly. However, it will be clear that the invention is applicable to periods of other length. Indeed, daily reports are preferably made, although it is also preferable to store CCC's only for complete months. The daily reports affect primarily the "current" window which, in the preferred embodiment, reports the CCC rating for the most current 50-day interval. When discussing the medical implementation herein, the terms daily and monthly will often be used, but unless it is otherwise clear from the context, what is being referred to is simply periodic reports (e.g., daily reports) which produce ratings for longer intervals comprising n period (such as monthly). In the example below, ratings will also be given which are identified as "current", and in the preferred embodiment of the invention, and according to the examples given, the "current" period means the information taken from the most current 50 days. It will be clear that the periods selected are for convenience, and are not intended as limitations, particularly limitations in the claims.

The words "mean" and "average" are often used in this specification in a somewhat interchangeable fashion. Typically, the broader term "average" is utilized, with the realization that often the composite statistic which is preferably being sought is the species, the straight arithmetic mean, of the broader genus average.

Those skilled in the art will appreciate the basis for determining targets from the peer group is the fact that the calibration standards do not have an absolute value. Thus, it is not like calibrating a scale against a 1 inch standard, in which the target will always be the 1 inch measurement of the standard. In the present context, the target value associated with the control sample will be the value which is measured by the norm of the mass population making the measurement.

Returning to FIG. 1, it will be seen that the central station 40 has a communication interface 41 coupled to the communication links 31. The typical means of reporting control data will be initiated from the laboratory, and thus the communication interface 41 must be available to establish a dial-up connection, to provide the necessary security checks, and then to receive data transmitted from the instrument locations. As an alternative, a period of the day may be set aside for communicating control data, and the communication session is to be initiated by the communication interface 41. A controlling central processor, schematically illustrated as 42, and shown without specific connections since it exercises supervisory control over all processing equipment at the central station, will be programmed to initiate the communication to each of the laboratories in a predetermined sequence, to receive and collect the control data.

Independently of whether the laboratories or the central station initiates the communication, control data will be communicated to the central station 40 by means of the communication channels 30, and the control data is collected and stored in a control data storage memory 44. The memory 44 is schematically divided into three sections 44*a*, 44*b*, 44*c* to signify that the control data (stored in the larger section 44*c*) will be associated with a laboratory (or instrument) identifier (stored in the section 44*a*), and the date of the report (stored in section 44*b*). When used with a typical three-control point calibration scheme, each word within the control data storage memory will hold a source identifier in the section 44*a*, the date in section 44*b*, and will have three slots available in the section 44*c* for holding the control data associated with each of the three calibration points. In a typical environment, provision will be made, of course, for other identifying information such as the lot number, reagent number, and other such information. Since that information is not important to an understanding of the present invention, it is not illustrated in the drawings.

A second module 46 is provided for storing information from which the control targets will be produced, and for processing the stored information for determining targets against which the control data of each laboratory will be compared. Thus, the target storage module 46 is illustrated in FIG. 1 as a large rectangle having a small rectangle 46*a* at the output thereof. The larger section 46 is intended to illustrate both the storage of the control data from which the target values are determined, and the actual determination of targets from the stored data. The output section 46*a* is intended to represent the control target values which are output for comparison with the laboratory control data. Thus, in the example being discussed, the section 46*a* will store three data points representing the low, medium and high targets (for each day) against which the low, medium and high control data for each laboratory will be compared over a predetermined interval.

The relative size of the storage modules 44, 46 is intended to suggest an important feature of the invention. In the typical quality control statistical processing environment, it is usual to process the information from all of the laboratories to generate averages to use as targets against which each laboratory is then measured. In accordance with the present invention, not all of the laboratories contribute to the determination of the targets, but only the subset of laboratories (the golden peer group) which have, in recent history, proven to be operating at high quality standards. However, every laboratory has an equal opportunity to compete for being selected in the golden peer group. The relative size of the rectangles indicates that the golden peer group is smaller than the peer group. The manner in which the golden peer group is selected on the basis of recent historical data will be described later.

In accordance with the invention, a concordance correlation coefficient module 47 is provided to compare the golden peer group targets from module 46 against the control data for each of the instruments taken from the control data storage module 44. The module 47 provides a single rating number for a given interval, which is rated against the CCC distribution for the entire peer group in evaluator 48, to provide a quality control rating for each instrument. The CCC comparator 47 and evaluator 48 produce a chart such as that illustrated at 49, and which will be described in greater detail below. The chart has a first section 49*a* which is a concordance chart of the instrument readings for each day of a given interval (such as a month or the last 50 days) plotted against the moving and fixed golden peer group standards for that same interval. A second section 49*b* will report numerically the concordance correlation coefficient for that instrument (and for the entire peer group) for the current period. Finally, a third section 49*c* will graphically illustrate the performance of the instrument with respect to the peer group. Section 49*c* is a plot of CCC with indicators for the average for the peer group and the one and two standard deviation (SD) lower limits from the average, and showing as points on the chart, the performance (CCC) of the laboratory with respect to the peer group. As will be described in greater detail in connection with FIG. 2, a wealth of information is contained in the chart 49, a chart which is much more meaningful than quality control charts which have been provided heretofore. In addition, it is also of significance that such a chart can be provided in very timely fashion according to the practice of the invention. In any event, it will be seen that the CCC report is shown by a connecting line 50 to be available to the communication interface 41 for transmission along the communication media 30 to each of the laboratories 21*a*–21*n*. Thus, if the laboratory is equipped with a personal computer and appropriate printer, the chart 49 which rates that laboratory against its peers can be transmitted electronically very shortly after it is generated, to be available in the laboratory that day. Indeed, it is preferred to perform a CCC evaluation and rating daily and to report the results electronically within a day of receipt of the control data. Alternatively, the line 50 is also connected across the communication link to the laboratories by the extension 50*a* illustrated in the drawings, the extension intending to illustrate the delivery of a paper chart 49 by way of mail, express or the like.

In accordance with a further aspect of the invention, a peer group selector 52 is connected to the correlation coefficient evaluator 48 and serves, on a periodic basis, such as monthly, to examine the average and standard deviation for the CCC's of all of the instruments. The peer group selector 52 functions not unlike a statistical filter in identifying those instruments which meet a standard which is selected to represent the "good performing" instruments, i.e., the golden peer group. In a preferred practice of the invention, the peer group selector 52 is configured to select all instruments within the lower one standard deviation limit of the average, and identify only those instruments as being within the golden peer group. Instruments within the one and two standard deviation level are separately identified but not otherwise used, neither in the golden peer group nor in a warning category. Those instruments identified as being below two standard deviations of the average are identified as out of control, and an out-of-control report 53 is issued and dispatched, either electronically or by express to the laboratory to indicate something is amiss. The out-of-control report 53 can be generated according to various standards, sometimes determined by the type of tests being run. For example, it may be typical to identify an instrument below the 2 SD level for one period as potentially out of control, and then after a second successive period below the 2 SD level, flag that instrument for an OOC report. Alternatively, an instrument performing between the 1 and 2 SD level for a given month and then falling below the 2 SD level for the next sequential month might be reported as out of control. The block 53 is simply intended to indicate that the statistical information is available, the standards can be set to meet the application, and the reports are generated according to whatever standards are established.

Figure 2:
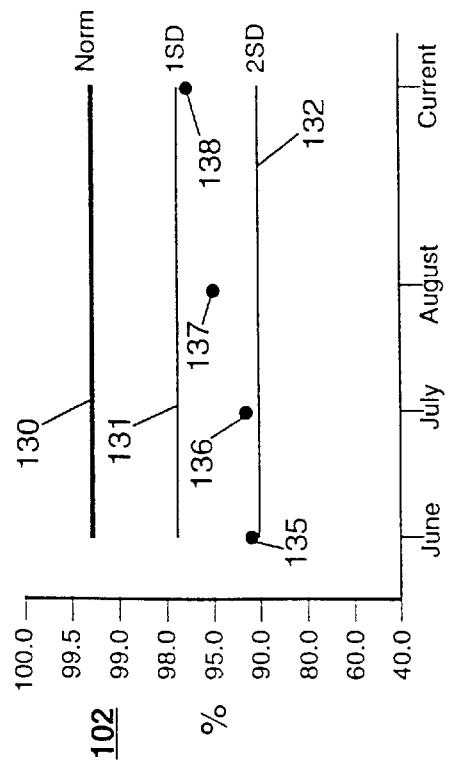
FIG. 2 is a typical report utilizing the concordance correlation coefficient produced in accordance with the present invention to report the performance of a given instrument with respect to its peers.
Figure 2:
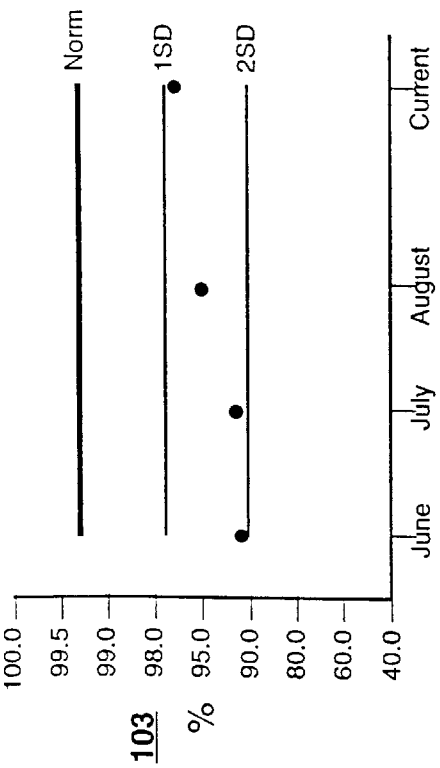
Figure 2:
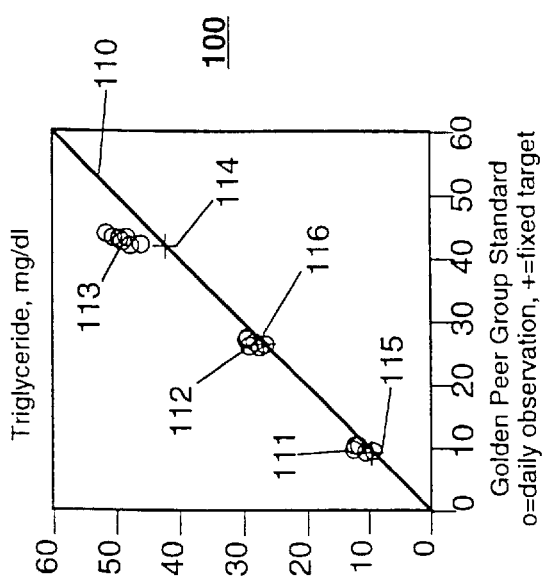

Before turning to FIG. 2, and describing the significance of the output chart, attention will first be directed to the general nature of the concordance correlation coefficient. The CCC according to the present invention is a measure of both precision and accuracy with respect to a target. In practicing the invention, the target, as noted above, is taken from the performance of a golden peer group. The golden peer group in turn consists of instruments within the larger group who maintain qualifying accuracy and precision during a predetermined recent interval, such as three months. In a preferred practice of the invention, two targets and two CCC indices are calculated. One of the CCC determinations is made against the moving target (for each day). The moving target is the mean or central norm of the golden peer group instruments for that day, and the control data for the instruments being evaluated is compared against that mean. The fixed target, on the other hand, is a constant and is the cumulative average of all of the golden peer group targets to that point in time. Thus, the moving target is a series of snapshots of the golden peer group standard for the period of the last month or the last 50 days. The fixed target, on the other hand, is the cumulative golden peer group standard since the beginning of a new lot of control material.

Figure 3:
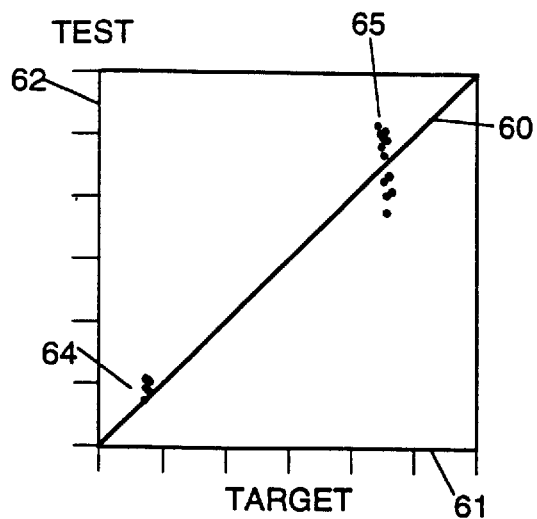
FIG. 3 is a diagram illustrating the concept of the concordance correlation coefficient.

In accordance with the invention, techniques are utilized to limit or diminish the influence of outliers or errors, in determining the targets, and a discussion of those techniques will be provided below in connection with FIG. 5. Assuming, however, that the targets are valid, the concordance correlation coefficient (CCC) is a measure of precision and accuracy of the readings of the individual instruments compared to those targets. Conceptually, the CCC evaluates how closely the observations over the desirable range (for example, low to high control levels) fall on the concordance line. The concordance line, as illustrated in FIG. 3, is a line 60 drawn on a plot of readings of the standard or target on the horizontal axis 61 and the test system being evaluated plotted as an ordinate 62. The concordance line 60 is a 45° line passing through the origin. Thus, if the control data readings of the instrument being evaluated match exactly those of the standard, the readings will be plotted directly on the 45° line 60. To the extent they deviate, they will be plotted away from the line 60. The concordance correlation coefficient is a measure of how well or how poorly the test data on the ordinate 62 conforms to the target data on the abscissa 61. It is measured on a scale of 0% (no agreement) to 100% (perfect agreement). Negative values are theoretically possible, if observed values decrease as a standard value increases, but that is not expected in the normal applications of the present invention. Typically, any CCC of less than 80% is unrealistically poor. The plot of FIG. 3 shows that for the low control values, a tightly knit cluster 64 of points is provided which fall closely on the concordance line 60. However, for the high control, an array of points 65 is provided which has a smaller cluster near the concordance line, but also a significant variation from that line. Those familiar with statistical analysis will appreciate that the plot of FIG. 3 typifies a standard in which the precision of the instrument is in doubt. A concentration of points which are mostly above (or mostly below) the concordance line may, on the contrary, indicate an instrument in which the accuracy is in doubt.

Figure 4:
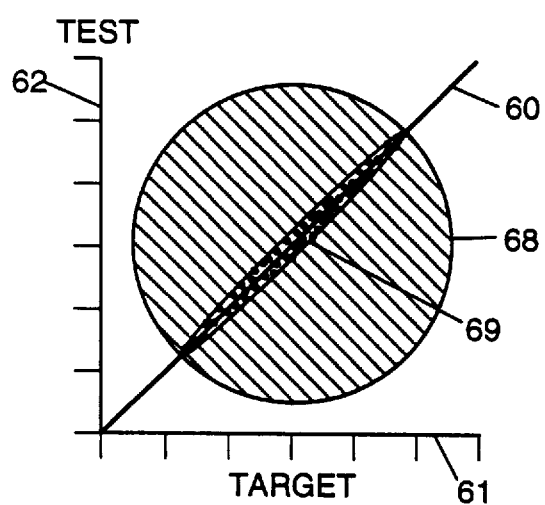
FIG. 4 is a diagram illustrating the geometric interpretation of the concordance correlation coefficient.

The CCC measures the squared distance of observations (data readings) from the concordance line 60. The distance is then standardized such that 100% represents a perfect agreement, and 0% represents no agreement. The geometric interpretation of the CCC is illustrated in FIG. 4. FIG. 4 shows the concordance line 60 and the plot of test data points against the target on the vertical and horizontal axes, respectively. The CCC can be considered to be the ratio of the hatched area in FIG. 4 (i.e., the majority of the area of the circle 68) to the area of the entire circle. Thus, the area 69 which represents the observations and which typically encompasses a small area of the circle which is near the concordance line 60 is subtracted from the entire area of the circle, and taken as a ratio with respect to the entire area to present a measure of the CCC, with 100% being perfect agreement, and 0% being perfect disagreement.

Conceptually, the CCC as it is utilized in the present invention, consists of a measure of precision multiplied by a measure of accuracy. The measure of precision is selected to be the Pearson Correlation Coefficient. The Pearson Correlation Coefficient evaluates how far the observations deviate from the best fit linear line through the observations. The measure of accuracy is identified as $C_b$, and that evaluates how far the best fit linear line through the observations deviates from the concordance line on a scale of 0% (far) to 100% (no deviation). The measure of accuracy, in turn, consists of a measure of location shift and a measure of scale shift. The measure of location shift, u, evaluates the absolute difference of the laboratory instrument average against the golden peer group average, relative to their standard deviations. The measure of scale shift, v, evaluates the ratio of the laboratory instrument standard deviation and the golden peer group standard deviation.

Those skilled in this art will appreciate a mathematical statement of the foregoing expressions, and that is provided in the following:

Let $y_{i1}, y_{i2}, \ldots, y_{iq_i}$, be the $q_i$ observations (across days) for control level i, i=1, 2; or i=1, 2, 3.

Let $x_{i1}, x_{i2}, \ldots, x_{iq_i}$, be the corresponding $q_i$ moving targets for $y_{i1}, y_{i2}, \ldots, y_{iq_i}$.

For fixed targets, $x_{i1}=x_{i2}=\ldots=x_{iq_i}$ for each i=1, 2; or i=1, 2, 3.

$$\text{Then } \bar{x} = \sum_i \sum_{j=1}^{q_i} x_{ij}/\sum_i q_i, \quad \bar{y} = \sum_i \sum_{j=1}^{q_i} y_{ij}/\sum_i q_i \tag{1}$$

$$s_x^2 = \sum_i \sum_{j=1}^{q_i} (x_{ij}-\bar{x})^2/\sum_i q_i, \quad s_y^2 = \sum_i \sum_{j=1}^{q_i} (y_{ij}-\bar{y})^2/\sum_i q_i \tag{2}$$

$$s_{xy} = \sum_i \sum_{j=1}^{q_i} (x_{ij}-\bar{x})(y_{ij}-\bar{y})/\sum_i q_i. \tag{3}$$

The accuracy is $$C_b=[v+1/v+u^2)/2]^{-1} \tag{4}$$

where $$u = (\bar{x}-\bar{y})/\sqrt{s_x * s_y} \tag{5}$$

$$v = s_x/s_y$$

The precision is $$r = s_{xy}/(s_x * s_y) \tag{6}$$

The concordance correlation coefficient is $$p_c = r * C_b \tag{7}$$

It will be seen from the foregoing that the concordance correlation coefficient can be evaluated against both fixed and moving targets. The moving target, as noted above, is simply an observation on a daily basis derived from the golden peer group. The fixed target, on the other hand, is the cumulative average of the golden peer group daily targets.

In the event either a moving target control point or a laboratory control point is missing, that pair of observations is not used in determining the CCC for that interval. Thus, it will be appreciated that although a CCC can be determined for an interval of say one month, the one month interval need not include 30 days. If data points are missing, the CCC can still be determined.

In addition, there must be at least two levels (preferably both the high and the low controls) in order determine the concordance statistics. If a laboratory instrument reports low and medium levels or medium and high levels, or has just one level of control, the control data for that laboratory for that day should also be deleted from the concordance determination.

It will also be noted that transformations will sometimes be used on the data, depending on the characteristics of the data. Those skilled in the art will appreciate the basis for such transformations, and the nature of the transformations to be used. Typically, when one attempts to rate a unit against its peers, it will be useful to determine the mean of all the peers and the 1 and 2 SD limits. If the data from the entire group is Gaussian (a bell-shaped curve), then it is known that 95% of the population will be within ±2 SD's of the mean. This result will not obtain, however, if the data from the group is skewed. Thus, when skewed data sets are present, as in the case of many medical applications, a transformation will be utilized early in the process (typically just after unit conversion) to convert the data to a Gaussian distribution. The process is then performed on the transformed data, including the determination of CCC for each laboratory, the determination of the mean CCC's for the entire peer group, and the 1 and 2 SD lower limits. That information is then anti-transformed and the information on the anti-transformed mean and 1 and 2 SD limits applies as it would to a Gaussian distribution.

It is well known that to produce a transform value represents a 1:1 mapping of the untransformed value into the transformed value using a continuous and monotonic function. The anti-transformation is the reverse process. The typical transformations which are utilized in accordance with data sets of this invention are expected to be the power function and the logarithmic function. The inverse hyperbolic tangent transformation is also used for the concordance correlation coefficient. Other transformations which may find use are the arcsine transformation and the logistic transformation. It is not believed necessary to list the equations for each of such transformations at this point, since those skilled in the art will appreciate which are to be used based on an analysis of the distribution of the original data and a further analysis of the distribution of the transformed data.

With that background, attention will again be turned to FIG. 2 for a discussion of the type of report which can be produced in accordance with the invention, and the significance of the information reported. Following consideration of the report and its content, attention will then be turned to FIG. 5 for a more complete disclosure of the system capable of functioning to produce information such as that reported in FIG. 2.

FIG. 2 contains a quantity of information displayed in different formats. The upper left-hand portion of the chart, identified as 100, is a plot of concordance for what is termed the current window (in the example, 50 successive days leading up to the report). It was noted above, that in the preferred example, reports are generated on a monthly basis, and correlation data is accumulated on a monthly basis along with a "current" period which comprises the last 50 days. The example of FIG. 2 illustrates the application of that approach.

Thus, and as will be described in greater detail below, the upper left portion of the chart 100 comprises a plot of the readings against target readings for the same period from the golden peer group, to produce the underlying data from which concordance determinations are made. The lower left-hand portion of the chart identified as 101 presents the actual calculated concordance data for the current period (i.e., the last 50 days). It will be seen that the lab instrument has concordance information (including both its precision and accuracy components) rated against moving and fixed targets. The moving target is the daily target produced by the golden peer group, whereas the fixed target is the cumulative target produced by the golden peer group. Also in the section 101 is the peer group concordance distribution indicating both the average and the lower first and second standard deviations. The peer group in this connection is the entire group, and the CCC for the instrument in question is merged with the CCC for all of the instruments to determine the average and also the 1 and 2 SD limits. The norm, 1 SD and 2 SD limits as set forth in the chart, are those which are plotted as horizontal lines in the graphical displays at the right of the chart.

The right-hand portion of the chart is a plot showing the CCC for the instrument in question for the last three months and also for the current period. It will be seen that the upper right-hand portion identified as 102 plots the CCC for the moving target, whereas the lower portion of the chart identified as 103 plots the CCC for the fixed target. In the illustration, the plots 102 and 103 are very similar. However, there are situations where performance will be substantially different when rated against the moving and fixed targets. For example, if there is a disparity between the concordance with moving target standard (102) and with fixed target standard (103), it generally indicates common factors, such as problems in the stability of the control materials, that are affecting all labs in the peer group. If such a disparity in CCC persists, an investigation of overall problems within the overall laboratory system should be undertaken.

Now turning in somewhat greater detail to the various portions of the chart of FIG. 2, it will be seen that the section 100 includes a concordance line 110, like that illustrated in FIG. 2. Plotted along with the concordance line are the data points for the instrument in question compared against the golden peer group standard, for the last 50 days. It will be seen that there is a large collection of data points 111 at the low control standard showing good agreement there, but an increasing disparity at the midpoint standard 112 and a fairly high disparity at the high control point 113. The groupings of circles 111, 112 and 113 indicate points, at which the laboratory reading for the day is compared against the target reading of the golden peer group for that day. Also shown in chart 100, and designated by the symbol "+", are indications for the fixed target. The fixed target is clearly seen for the high control 114 and underlies the data points and is partly discernible for the low 115 and intermediate 116 controls.

For the 50 days in question (and also for the most recent month), the concordance correlation coefficient is determined for a comparison of the readings against the golden peer group as illustrated in the plot 100. As noted previously, equation 1, in its determination of the $\bar{y}$ information determines the average across days for the respective control levels, whereas the $\bar{x}$ information determines the average of the daily moving targets for the y observations across the same period of days. Thus, the computations will be done for both the 50-day current interval as well as for the last month. Having computed the factors of equations 2 and 3, a determination of the accuracy $C_b$ is made according to expression 4. Precision is then determined according to expression 6, and the products are multiplied as indicated in expression 7 to provide a concordance correlation coefficient (CCC) which is a product of the accuracy and precision factors.

The actual CCC numbers are reported in the section of FIG. 2 indicated at 101. A "lab-instrument" section of the chart 120 has a first column 121 for reporting the concordance correlation coefficient for the current period. It is seen that the coefficient with respect to the moving target is reported at 96.2%, whereas with respect to the fixed target, it is determined to be 96.3%. In the foregoing, it will be appreciated that the moving target is the target established by the golden peer group for each day, and changes on a daily basis as the observations of the golden peer group change. The fixed target is the average of the golden peer group over time, such as for the period of time since the beginning of the current control lot. That period can extend for months. The average is continually updated as the peer group reports are received, and the fixed target (the average at the end of the period) is taken as the target for each day. Thus, with respect to determination of $\bar{x}$ in equation 1 for the fixed target, the x for any of the three control points remains the same over the entire period, and the number of times the x reading is utilized is determined by the number of observations for the laboratory in question.

It will also be seen in FIG. 2 in the chart section 101 that a column 122 is provided indicating the precision measure of the concordance correlation coefficient (that determined by expression 6), and a second column 123 reports the accuracy measure (that determined by expression 4). The product of the factors 122, 123 yields the concordance correlation coefficient reported in column 121.

The section of the chart 101 also includes peer group distribution information. It will be seen that the peer group has a norm over the three month period in question which is reported in column 125, and the norm is also taken with respect to the moving and fixed targets. Thus, all instruments in the peer group for the month of, for example, June, have a average CCC, those for July and August have different average, and the average of those three averages (irrespective of the identity of the instruments which produce them) is reported as the norm in column 125. The lower standard deviation levels are reported in column 126 for 1 SD and column 127 for 2 SD's.

Focusing on section 102, it will be seen that the CCC-related performance of the instrument is reported against the performance of the peer group for the three months in question as well as for the current period. The upper portion of the chart 102 reports the results when taken in comparison with the moving target. The norm line 130 is the information taken from column 125, that is, the 99.1% CCC for the peer group against the moving target, and the one SD and two SD limits taken from columns 126 and 127 are also plotted as horizontal lines 131, 132. Included on the chart are marks (dots in this case) which indicate the performance of the instrument being evaluated as compared to the peer group norm. It is seen that a series of dots 135, 136, 137 rate the laboratory against the peer group for the last three months, and a further dot 138 rates the current 50-day interval in comparison to the peer group.

Section 103 of the plot provides the same information but with respect to the fixed target. In view of the discussion of the fixed target given above, it is not believed necessary to describe the chart 103 in greater detail except to point out that the norm, one SD and two SD horizontal lines are taken from the columns 125, 126 and 127 according to the fixed target peer group statistics, and the dots which indicate the performance of the instrument against those targets are taken from column 121 and the similar information produced for the July and August intervals.

The comparison of the CCC for the instrument against the CCC distribution for all of the instruments (the norm and SD levels) is of significance in the present invention because taken on its own, the CCC is not completely meaningful. For example, a CCC of 98% can be accurate beyond expectations for some types of measurements, but below acceptable levels for others. Thus, it is not only important to determine the CCC for an instrument in question, but also to evaluate the CCC's for the entire peer group to determine a mean or average and the standard deviation levels, and armed with that information, a given laboratory will have a very good indicator of the quality of its performance. Considering that distribution of the CCC's over the peer with a proper transformation is substantially Gaussian, then anti-transformed, the norm and 1 and 2 SD limits shown in FIG. 2 can be interpreted as a Gaussian distribution to assist in evaluating how an instrument is performing with respect to its peers. For example, considering that a one-sided distribution is being evaluated, it is known that 97.5% of the population will lie within 2 SD's of the norm.

Figure 5:
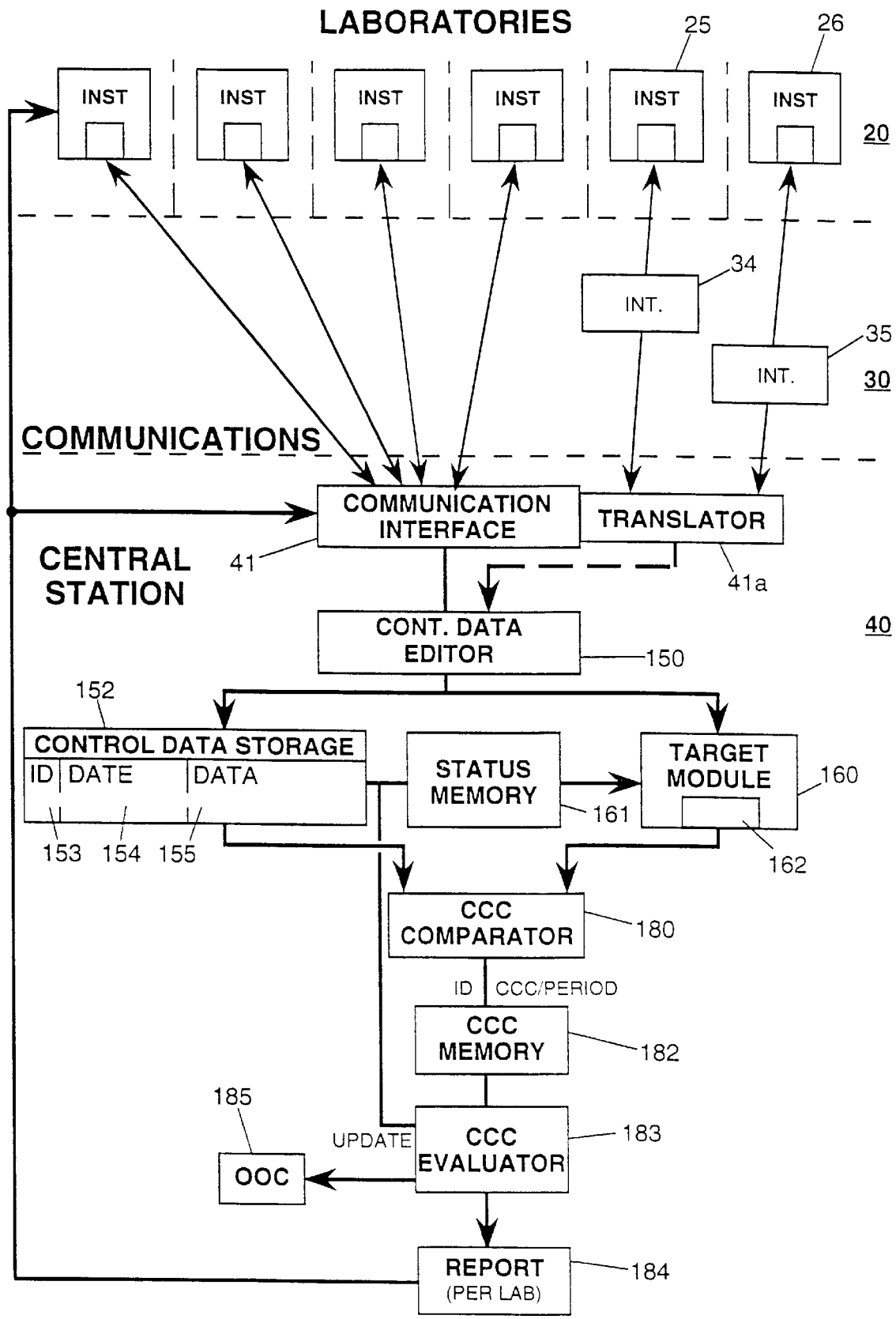
FIG. 5 is a detailed block diagram illustrating a system incorporating the present invention.

Turning now to FIG. 5, there is illustrated in greater detail than in FIG. 1 a system for practice of the present invention. As in FIG. 1, the system of FIG. 5 is broken down into three areas, an area 30 comprising a large group of geographically distributed laboratories 21a–21n, with laboratory instruments 22a–22n. The instruments have communication capability 24.

Also like FIG. 1, a communication system 30 comprises communication links 31a–31n which allow the transfer of data or other information between the communication modems 24 of the instruments and a communication interface 41 of the central station 40.

FIG. 5 also illustrates a group of instruments 25, 26 which report control data to the central station 40 but by means other than the direct communication links 31 described in connection with instruments 22. That is illustrated by incorporation of an interface 34, 35 in the communication link 30, and a translator 41a associated with the communication interface 41 and having a dotted line output to the control data editor block. The instruments 25, 26 are intended to represent the condition where control data is not reported electronically on a daily basis but can be summarized and reported by means other than electronic communications. Thus, for example, the laboratory 25 may collect control data for a week. Such data may be transmitted directly over a communication link to the translator 41a, or the interface 34 may indicate a mail conversion of paper data being transmitted to the central station. Instrument 26 illustrates a further condition where data may be collected and transmitted on a daily basis, but for whatever reason not electronically, by means of a paper interface 35. In both cases, the translator 41*a* will input the data so that the laboratories 25, 26 can be rated, but will typically exclude the data from the golden peer group determination. Thus, the laboratories 25, 26 may participate in the overall rating scheme, but because of the manner in which the data is reported, will typically be excluded from consideration for the golden peer group. Should the interfaces 34, 35 or the means of reporting be determined to be adequately accurate and timely, it is of course possible to include the laboratories 25, 26 within the golden peer group should that be desired.

A control data editor 150 cooperates with the communication interface 41 to assure that the data received from the instruments 24*a*–24*n* is valid control data and should be used in the quality control evaluation. In some systems, the instruments 24*a*–24*n* may transmit actual patient data to the central station, and the control data editor 150 is capable of distinguishing patient data from control data, and routing the former elsewhere. As a further example, the laboratory may submit a file of control data, but with a header indicating that the control data is corrupted and should not be used in the quality control evaluation. The control data editor 150 will also route such data to a special file, and prevent it from being routed to the other elements illustrated in FIG. 5.

When a sending station, which has identified itself, transmits appropriate control data, that will be recognized by the editor 150, and the control data along with the identification of the laboratory or instrument and the date associated with the data will be routed to other portions of the system of FIG. 5. Most appropriately, the control data will be routed to a control data storage area or memory 152. The memory is shown as having three sections 153, 154, 155. The section 153 represents storage locations for the identity of the instrument which has transmitted the control data. The section 154 represents storage for the date associated with the control data. And the section 155 represents the storage area for the control data itself. It will be recalled from the foregoing that at least low and high control point are transmitted, and in many cases there will also be an intermediate control data point.

In certain implementations of the invention, and in the one currently preferred, there will be only one control data entry per instrument per day which will be entered in the control data storage memory 152. Other control data can be submitted by the instrument and will be routed to another good control data storage register, and will be used in preparing typical statistics as have been prepared in the past. However, in this preferred implementation of the invention, in determining both the golden peer group against which the instruments are to be evaluated, and in evaluating each instrument against the golden peer group, only one data set per day is utilized per instrument, and that is selected as the first control data set transmitted on any given day.

In other implementations of the invention, the first control data set for the day from each instrument will be used in establishing the golden peer group targets, but all valid control data points from that instrument transmitted in a given day can be used in determining performance for that day, to be evaluated against the golden peer group. It is currently believed that there will be less possibility for manipulation of the results if only the single set of control data for each instrument per day is utilized, and thus the former system is preferred.

In addition to storing the control data along with the identification information in the control data storage module 152, the control data editor 150 also passes the data to its target module 160. The target module 160 preferably is presented with the data as it is received so that certain of the data processing steps needed for determining fixed and moving targets can be accomplished as early in the process as possible. Preferably, these steps establish the moving target for each instrument and also accumulate the fixed target values for each instrument, such that the fixed and moving targets for each instrument are available at the end of a period when it is desired to perform a CCC determination. At that point, it will only be necessary to process the data across instruments to determine the final fixed and moving targets, as will be described below.

Briefly, the target module 160 accepts the data from the individual instruments, processes the per-instrument moving targets and cumulative targets, responds to a instrument status memory 161 which identifies the instruments within the golden peer group, and when it is desired to produce golden peer group targets, performs certain processing steps in order to load into an output register 162 the moving targets and fixed targets for the golden peer group. The moving target will, of course, be on a daily basis, with the target changing on a day-by-day basis depending on the performance of the golden peer group. The fixed target will be a single fixed target for all of the instruments of the golden peer group accumulated over the period in question.

Figure 6:
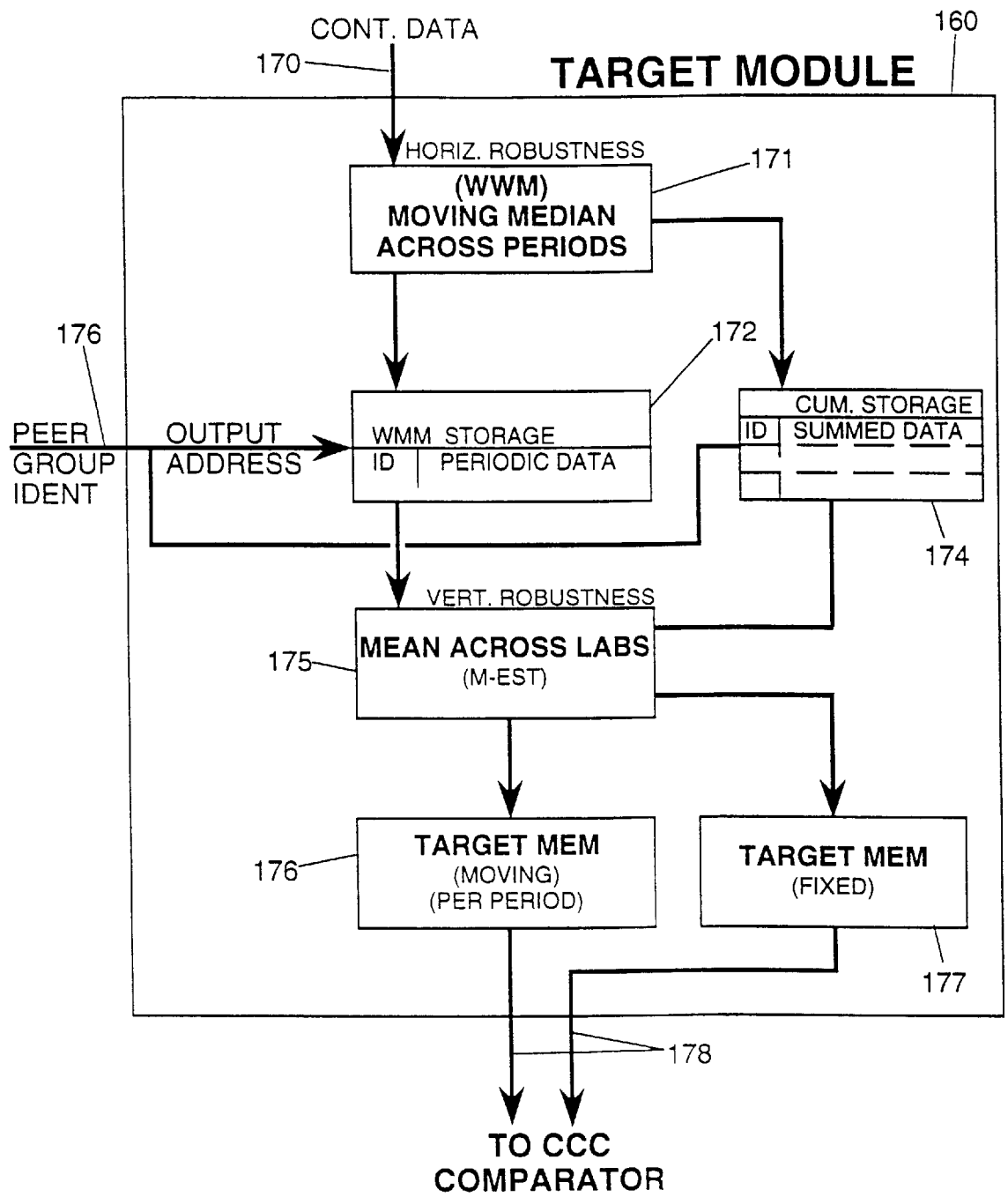
FIG. 6 is a block diagram illustrating the details of an implementation of a target module of the system of FIG. 5.

For a better understanding of the structure and operation of the target module 160, reference will now be made to FIG. 6 which illustrates certain of the components which make up such module. It will be seen that an input line 170 bears the control data which is reported by each instrument (along with its identification and date information). That data is conducted to a module 171 which processes the observations from each instrument across a predetermined time interval in order to provide the system with horizontal robustness, that is, robustness across time within any given instrument. In the preferred implementation of the invention, the module 171 determines a weekly moving median (WMM) for each of the instruments, and outputs that median on a daily basis to a weekly moving median storage memory 172. As will be described in greater detail below, the memory 172 has a set of memory locations for each instrument, and stores information in the memory relating to recent control reading (for each of the control points). The median value from the small group of stored data points is selected as the output for the channel for any particular day in question. The ability to input a relatively small number of days worth of information, and to select the median from that information, tends to provide horizontal robustness by eliminating or substantially reducing the effect of outliers. For example, if one data point is considerably higher than the others, it will continue to occupy its place in the moving median for the period of time covered by the median, but it will never be reported out as the median value, it will always be on the high side of the n reading in the moving window. The preferred manner in which the moving window is applied is to establish a weekly moving median for each of the control points for each of the instruments, and to select a central or median reading from that window as the output for any given day. It will be appreciated that there are times when the instrument will not report data on any particular day, and thus the weekly moving window may have less than 7 readings within it. Accordingly, the output of the window is taken, and whenever there are an odd number of readings within the window as being the central value, i.e., the observation whose magnitude falls in the middle of the range, there being an even number above it and an even number below it. When there are an even number of samples within the window, the output is taken as the average of the two central samples.

The storage of incoming observations (or data) and their processing to determine the weekly moving median for any given day, and for any channel, will be better understood from the following.

Let $x_1, x_2, \ldots, x_p$ be the observations of the $p^{th}$ day from the beginning of a new lot. Let $m_1, m_2, \ldots, m_p$ be the weekly moving median (WMM) of the $p^{th}$ day from the beginning of a new lot. Then:

---

$m_1 = x_1$,
$m_2$ = middle value of $x_1$ thru $x_3$,
$m_3$ = middle value of $x_1$ thru $x_5$,
$m_4$ = middle value of $x_1$ thru $x_7$,
$m_5$ = middle value of $x_2$ thru $x_8$,
$m_6$ = middle value of $x_3$ thru $x_9$,
.
.
.
$m_{p-3}$ = middle value of $x_{p-6}$ thru $x_p$.

---

The middle value is the value such that the number of observations smaller, and the number of observations larger, than the value are equal.

For computational efficiency for calculating $m_i$, i=1, 2, . . . , p, sorted data from the moving previous 6 days is stored and sorted. This is done so that a complete sorting of 7 observations need not be performed. The following describes the sequence:

Let $M_p$ be the weekly moving median of the day p-6 to day p.

On day 3, sort the 3 observations and let $v_1$ be the smallest, $v_2$ be the middle value, and $v_3$ be the largest. Then $M_3=v_2$. Store this $M_3$ as the median in memory 172 for the particular laboratory, $v_1$ as value 1, $v_2$ as value 2 and $v_3$ as value 3.

On day 4, compare $x_4$ to values 1, 2 and 3 saved earlier. If $x_4$ is between $v_1$ and $v_2$, then $M_4$=the average of $x_4$ and $v_2$, value 1=$v_1$, value 2=$x_4$, value 3=$v_2$ and value 4=$v_3$. If $x_4$ is between $v_2$ and $v_3$ or $x_4$ is greater than $v_3$, same logic is applied.

On day 5, update the order and save all 5 sorted values and the middle value as the median ($M_5$).

On day 6, update the order and save all 6 sorted values and store the average of the 2 middle values as the median ($M_6$).

For day i beginning on day 7, update the order and store the middle value as the median. Save the 6 sorted values into value 1 through value 6 in memory 172 after dropping the day i-6 value.

If a value is missing on any calendar day, the median will be computed based on the available observations. The median will always be the middle value if all 7 days data are available, or if 5 days or 3 days data are available. The median will be the average of the 2 middle values if an even number of observations are available. When retrieving the weekly moving median $M_i$, the $M_i$'s should be repositioned by making $m_{i-3}=M_i$, . . . etc.

Thus, for each instrument, the first set of control samples for the day is passed to the weekly moving median module 171, and a process as described above is performed to select the central value for the current 7 day period. That value (for each of the low, medium and high control points) is output and stored in the memory 172, along with the identification for the instrument which produced it. It is also convenient to store the presorted 7 day values for updating of the weekly moving median on a daily basis. Thus, for any given day, when a sample is produced by a particular instrument, the 7 sorted values for the period are updated by deleting the oldest one, adding a new one, finding the middle value, and reporting that value as the weekly moving median for that day.

As noted above, it is also desirable to maintain a cumulative fixed target, for determination of the CCC with respect to a fixed target (as opposed to the moving target of the weekly moving median information). To that end, the weekly moving median which is produced by the module 171 in concert with the memory 172 on a daily basis, is also reported to and stored in a cumulating memory section 174.

For the cumulative fixed target, let $M_{c,i}$ be the cumulative average of WMM from the beginning of a new lot to day i. For each incoming WMM, denoted by $M_{i+1}$, the $M_{c,i+1}$ will be updated in memory 174 by computing $$M_{c,i+1}=(iM_{c,i}+M_{i+1})/(i+1).$$

Thus, the cumulative total is simply updated each day when a new daily median is produced by multiplying the current cumulative median by the number of observations which went to make it up, adding to it the new cumulative median, and dividing the sum by the number of samples which have gone to make up the new weekly moving median, i.e., i+1. In the preferred system, the cumulative median for use as a fixed target continues to accumulate for so long as a given lot of control material is utilized. Whenever a new lot is shipped to the laboratories and on a given day all of the laboratories begin using the new lot of control material, on that same day the cumulative weekly moving median registers are cleared, and a new cumulative median fixed target is initiated.

Thus, returning to FIG. 6, it will be seen that whenever control data which is to be used in determining the golden peer group is received, it is processed by the weekly moving median module 171 to store in memory 172, for each channel, and for each day, the WMM targets for that day. Preferably, samples for each day of the week are stored and sorted in the memory 172, so that when the sample for the next day is produced, it is a simple matter of resorting to determine the WMM target for that day. At the same time, the median for each instrument is accumulated in the memory 174 to provide a fixed target. The samples in the memory 172 are stored on a day-by-day basis for each instrument such that a target is available for each day in an interval of n days for which a concordance correlation coefficient is to be determined. Thus, in the preferred example, where the CCC is determined both on a calendar monthly basis and for the most recent 50 days, the information which is read out of the memory 172 for the moving target is determined by the period for which the CCC is to be determined. It is therefore important that the day for which the data is appropriate is also recorded as well as the identification for the instrument.

By way of contrast, the memory 174 for the cumulative data is smaller in that it need only store the cumulative to that date median of the weekly moving medians on a instrument-by-instrument basis.

As pointed out in detail above, the weekly moving median technique provides horizontal robustness across time for each instrument by minimizing or substantially eliminating the effect of outliers or erroneous data readings. To the extent that a single outlier or single erroneous data reading is present, it will move through the window of the weekly moving median without ever actually being reported out as the median itself. This, of course, is in contrast to the control data stored in memory 152, where the outliers are stored and later compared to the targets to produce a CCC.

In practicing the invention, means are also provided for assuring vertical robustness across instruments by a similar statistical technique which produces a target average for all of the instruments, while at the same time reducing the effect of outliers and erroneous reading for individual instruments. To that end, a vertical robustness module 175 is provided to produce a mean (or average) across instruments. The module 175 has as inputs, the weekly moving median memory 172 and the cumulative memory 174. The information from those memories is processed individually. When the module 175 operates on the information from the weekly moving median module 172, it produces a target value for each day, which changes by the day. In contrast, when the vertical robustness module 175 operates on the fixed target cumulative memory 174, it produces a single target to use for every day over the interval in question.

In accordance with the invention, not all of the instruments which are being monitored for quality control purpose contribute to the target values, but only those instruments which have operated within a predetermined standard of "goodness" for a predetermined period of time. Returning briefly to FIG. 5, it is seen that a status memory 161 is coupled to target module 160. Means for updating the status memory 161 will be described below. Suffice it to say for the moment, that the memory 161 maintains an identifier for each instrument within the overall group. Those instruments which have operated according to the standards established for the golden peer group are separately identified, and the module 161 by virtue of its addressing connection to the target module 160 addresses only the golden peer group in determining the target values, be they the moving target or the fixed target, for the correlation coefficient computation. Thus, returning to FIG. 6, it is seen that the module 172 has a peer group identification input 176 which is derived from the status memory 161. It is noted that the function of the input 176 is to produce output addresses for the memory module 172. Thus, when it is desired to compute a concordance correlation coefficient for a given period, the status memory 161 sequentially reads out the identity of each instrument within the golden peer group. That information imposes a part of the output address on the storage module 172. The module 172 thereupon reads out the control points for each of the golden peer group laboratories for each day in question, to produce a target value for each day. Thus, taking first the low control point, and considering that 50 sequential days will be required for 50 sequential targets, the status memory 161 reads out the address of the first instrument within the golden peer group, and for the first day it reads out its low control point sample. The line 176 is incremented to the next instrument within the golden peer group, and all of the low control group observations for the golden peer group for the day in question are read out and imposed upon the module 175 which produces an average across instruments. Preferably, a two-step M-estimator technique is utilized. In summary, the observations from each of the instruments within the golden peer group is combined for the given day and for the given control point to produce a target value for that day for that control point which is based on the observations of all of the instruments within the golden peer group, with the two-step M-estimator providing vertical robustness by eliminating or minimizing the effect of erroneous data or outliers.

The two-step M-estimator technique, as will be appreciated by those skilled in the art, can be described as follows:

Let $x_1, x_2, \ldots, x_n$ be the n observations (number of instruments) in the golden peer group, then compute the average and the standard deviation as conventional. Let the weight, for $i=1, 2, \ldots, n$, be $$w_i = \tanh\left(\frac{x_i - \bar{x}}{s}\right) / \left(\frac{x_i - \bar{x}}{s}\right) \quad (9)$$

where tanh (Å) is the hyperbolic tangent function, and can be computed by $$\tanh(y) = \frac{e^y - e^{-y}}{e^y + e^{-y}}. \quad (10)$$

and the one-step M-estimation of the average becomes $$\hat{\mu}_1 = \sum_{i=1}^{n} w_i x_i / \sum_{i=1}^{n} w_i \quad (11)$$

Then the weight is recalculated as $$w_i = \tanh\left(\frac{x_i - \hat{\mu}_1}{x}\right) / \left(\frac{x_i - \hat{\mu}_1}{s}\right) \quad (12)$$

The one-step M-estimation of the scale becomes $$\hat{\sigma}_1 = \sqrt{\frac{1}{n-1} \sum_{i=1}^{n} w_i (x_i - \hat{\mu}_1)^2} \quad (13)$$

The weight is again recalculated as $$w_i = \tanh\left(\frac{x_i - \hat{\mu}_1}{\hat{\sigma}_1}\right) / \left(\frac{x_i - \hat{\mu}_1}{\hat{\sigma}_1}\right) \quad (14)$$

The two-step M-estimation of the mean becomes $$\hat{\mu}_2 = \sum_{i=1}^{n} w_i x_i / \sum_{i=1}^{n} w_i \quad (15)$$

The weight is again recalculated as $$w_i = \tanh\left(\frac{x_i - \hat{\mu}_2}{\hat{\sigma}_1}\right) / \left(\frac{x_i - \hat{\mu}_2}{\hat{\sigma}_1}\right) \quad (16)$$

The two-step M-estimation of the standard deviation becomes $$\hat{\sigma}_2 = \sqrt{\frac{2}{n-1} \sum_{i=1}^{n} w_i (x_i - \hat{\mu}_2)^2} \quad (17)$$

Thus, the average value for all of the instruments for a given control point and for a given day is determined by expression 15 and that is stored in the output register 162 as the moving target for that control point for that day. The M-estimation technique outlined above is applied to each control point for each day among all of the peer group instruments by continuing to read the information out of the memory 172, to produce a moving target for each control point for each day.

In a similar fashion, fixed targets are produced for low, medium and high control points by using the cumulative (to that date) median from each of the golden peer group instruments combined as in equation 15 to determine low, medium and high target fixed values. In FIG. 6, the fixed target values (low, medium and high) are stored in memory 177, and the daily moving targets (for each of the low, medium and high targets) are stored in the larger memory section 176. It will be seen that output lines 178 are coupled to the CCC comparator for producing a measure by which each instrument is compared to the golden peer group, and to derive from that a measure of how the instrument compares to all of the peers in the group.

Having thus stored control data from all of the instruments to be rated in the quality control system (such storage being accomplished in the memory 152 in the illustrative system), and having determined target value against which the control data is to be compared (such target values having been stored in memory section 162 in the illustrative embodiment), in accordance with the invention, a comparison is made between the control data for the instruments and the targets from the golden peer group to produce a single rating for each instrument which is a measure of both precision and accuracy. To that end, a concordance correlation coefficient comparator 180 receives the output of memory 162 and memory 152, and performs a comparison to produce a concordance rating for each instrument. The comparison was described in connection with expressions 1–7 earlier in this application, and the comparison was graphically illustrated in connection with FIGS. 2–4. Referring specifically to FIG. 2, in the chart 100, the comparison being made is for the low, medium and high control points from each instrument against the moving targets for the days in question. Even though the effect of outliers was eliminated in determining the targets, the outliers were stored as control data in memory 152, and these actual data points are compared in the CCC determination. The chart 100 illustrates the comparison having been made for 50 days. The output as noted above is a measure of precision (the Pearson Correlation Coefficient) and accuracy (denoted $C_b$), the product of which is the CCC. That number is produced for each instrument for the current 50-day interval and also for the calendar month which has ended most recently. The output for each instrument is passed to a memory 182 where both the most recent monthly value as well as the current window (i.e., the last 50 days) are stored, along with an identification of the periods for which they are stored. During prior monthly computations, the CCC for prior months has already been entered into and stored in the memory 182, which maintains a continuing record of the CCC for each instrument being rated.

It was noted above that the CCC is also determined with respect to fixed targets, and the fixed targets are read out of the memory 162 for comparison against the control data for each instrument, and a similar CCC determination made. That information is also stored in the memory 182.

Figure 7:
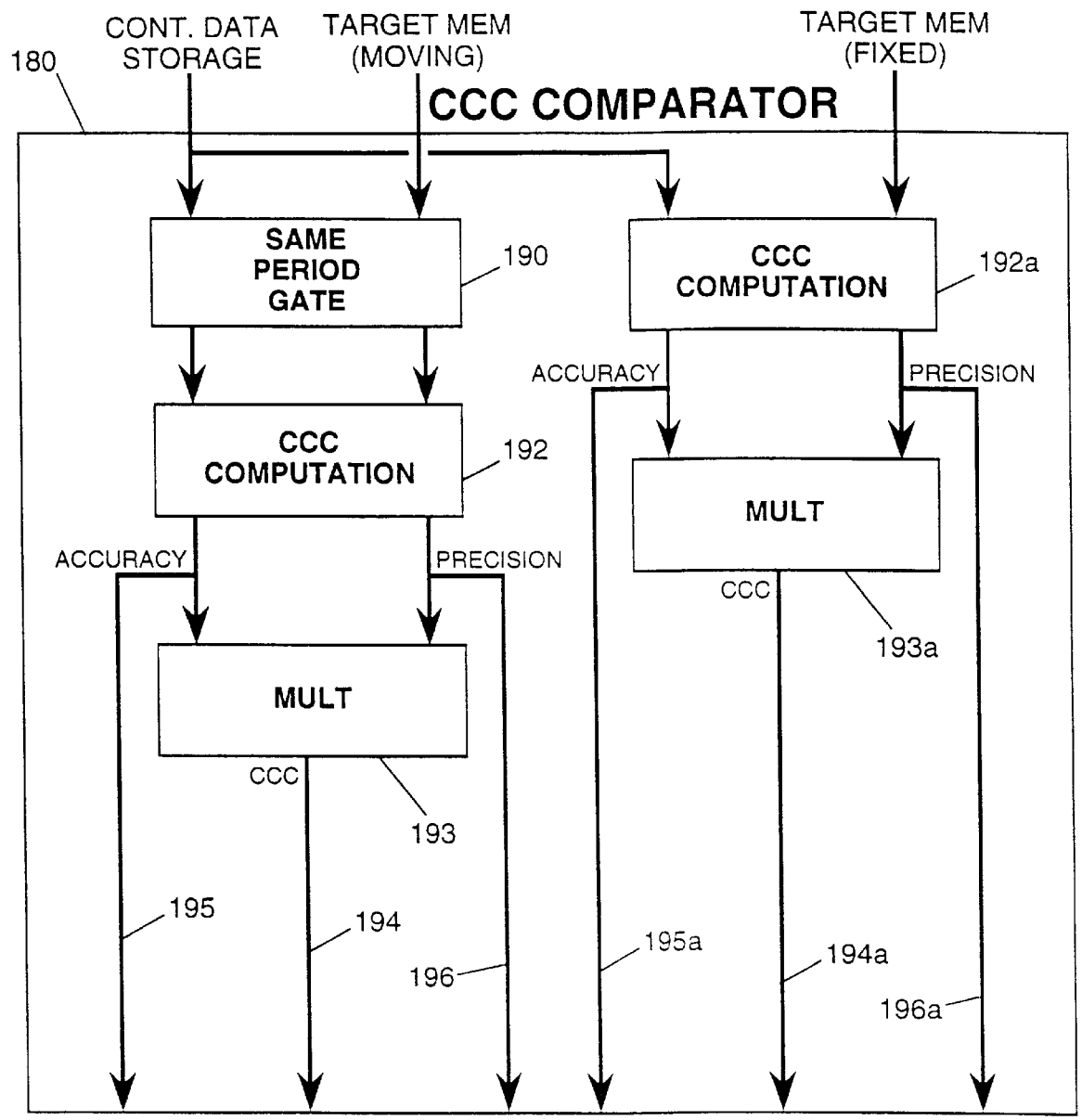
FIG. 7 is a diagram illustrating the details of one implementation of a CCC comparator for the system of FIG. 5.

The correlation coefficient comparator 180 of FIG. 5 is illustrated in somewhat greater detail in FIG. 7. First of all, the information from the control data storage register 152 and from the moving target register 162, is applied to a gating circuit 190. The gating circuit simply determines whether entries are available for the same day from both sources. If there are, then the observations (both the instrument observation and the moving target against which it is to be compared), are passed to a module 192 to perform the CCC computation. If there are not entries from both sources (typically when the instrument has not reported a control value for that day), then the gate 190 will not pass paired samples to the CCC computation module 192, and that day will be eliminated from the computation. The CCC computation module 192 performs the computations identified as expressions 1–6 in the foregoing, and the multiplier 193 produces a CCC rating on an output line 194 as well as accuracy 195 and precision 196 factors on the corresponding output lines. That is the information which is passed to the CCC evaluator 183 (FIG. 5) and ultimately used in the plot of FIG. 2.

The CCC computation 192a against the fixed target is performed by a module like module 192, except that there is no same period gate 190 which precedes the computation. The control data storage input is coupled to the input of the CCC computation module 192a, and the number of days for which samples are available is determined as those samples are input. The fixed target is also input to the module 192a, and that fixed target is applied in expressions 1–3 the number of times for which samples are available. The computation performed by the module 192a produces accuracy and precision factors as described in connection with module 192, which are applied through a multiplier 193a to produce the CCC with respect to the fixed targets.

In accordance with an important aspect of the invention, the CCC information, before it is produced in a report 184, is compared with the CCC distribution of all instruments in the system. Thus, while the CCC is determined with respect to a golden peer group, the report of the CCC with respect to the universe of the instruments is made with respect to the CCC distribution of all instruments in the system, i.e., the entire peer group, not just the golden peer group.

It will be appreciated by those skilled in this art that a CCC at a given level, such as 98%, does not have relative meaning in and of itself. For example, in certain applications, such as triglycerides, a CCC of 98% may be very poor. In contrast, 98% reading in connection with other tests may be extremely favorable. Thus, in accordance with the invention, the CCC value for an instrument is reported and in addition the CCC is rated against the CCC's distribution of all laboratories in the system.

To that end, a CCC evaluator 183 is connected to the CCC memory 182 for the purpose of evaluating the CCC and producing summary statistics. The average of the CCC's for all instruments for each period is determined. Thus, there will be a monthly average for each month of the year, as well as a current average for the 50-day snapshot preceding the current report. Along with the average, the one and two SD lower limits are computed. Information is thus available on the CCC distribution of all instruments in the peer group. This is typically determined by the average/norm and the standard deviation from the average/norm. It is the norm and one and two SD limits which are plotted as horizontal lines on the charts 102, 103 of FIG. 2. By first generating a highly precise CCC with respect to the golden peer group, and then subsequently by rating the CCC's for each instrument against the entire peer group of instruments, a comprehensive but simple report is made showing where each individual instrument stands with respect to the universe of instruments performing the same test procedure.

The module 183 also serves a function in selecting the golden peer group for a subsequent period. A standard can be programmed into the module 184. In the currently preferred practice of the invention, that standard identifies all instruments operating within the one SD limit of the norm for the prior three months, and those are identified as the "good performing" instruments within the universe of instruments. Each of those instruments is identified by setting a flag or the like in the memory 161. Thus, in the subsequent period, when the target module 160 is operated to produce a median across instruments for the golden peer group, the golden peer group will be identified as the instruments for which flags have been set in the module 161.

It was also noted in connection with FIG. 1, that the CCC evaluator 183 can also produce other reports, such as an out-of-control report, for instruments which have performed below standards for an identifiable period of time. Such out-of-control reports are indicated generally by the block 185, but will not be described here in greater detail.

Figure 8A:
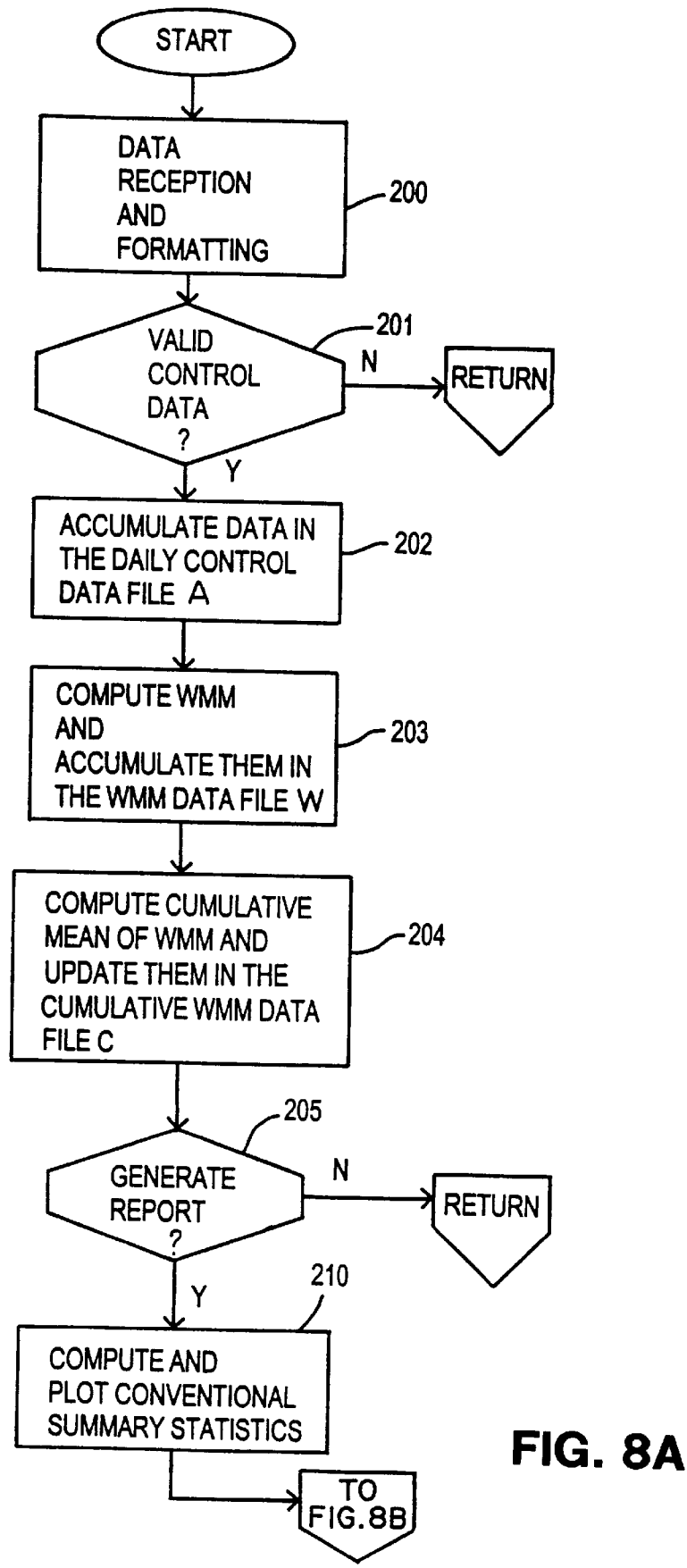
FIGS. 8A–8C are flow charts illustrating the process flow for certain aspects of the system of FIG. 5.
Figure 8B:
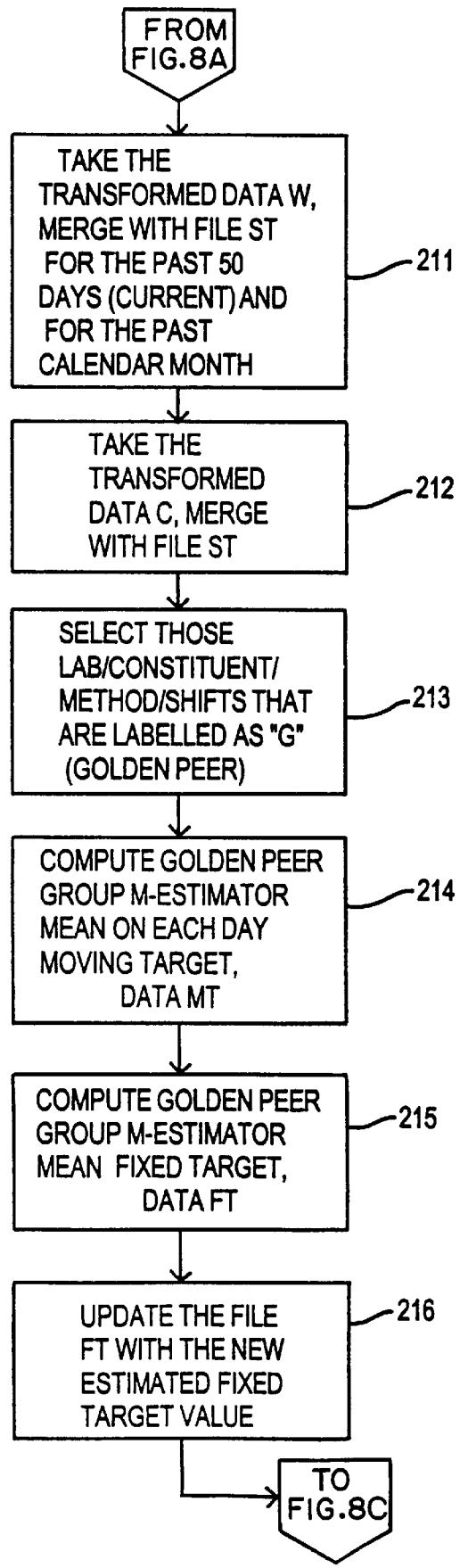
Figure 8C:
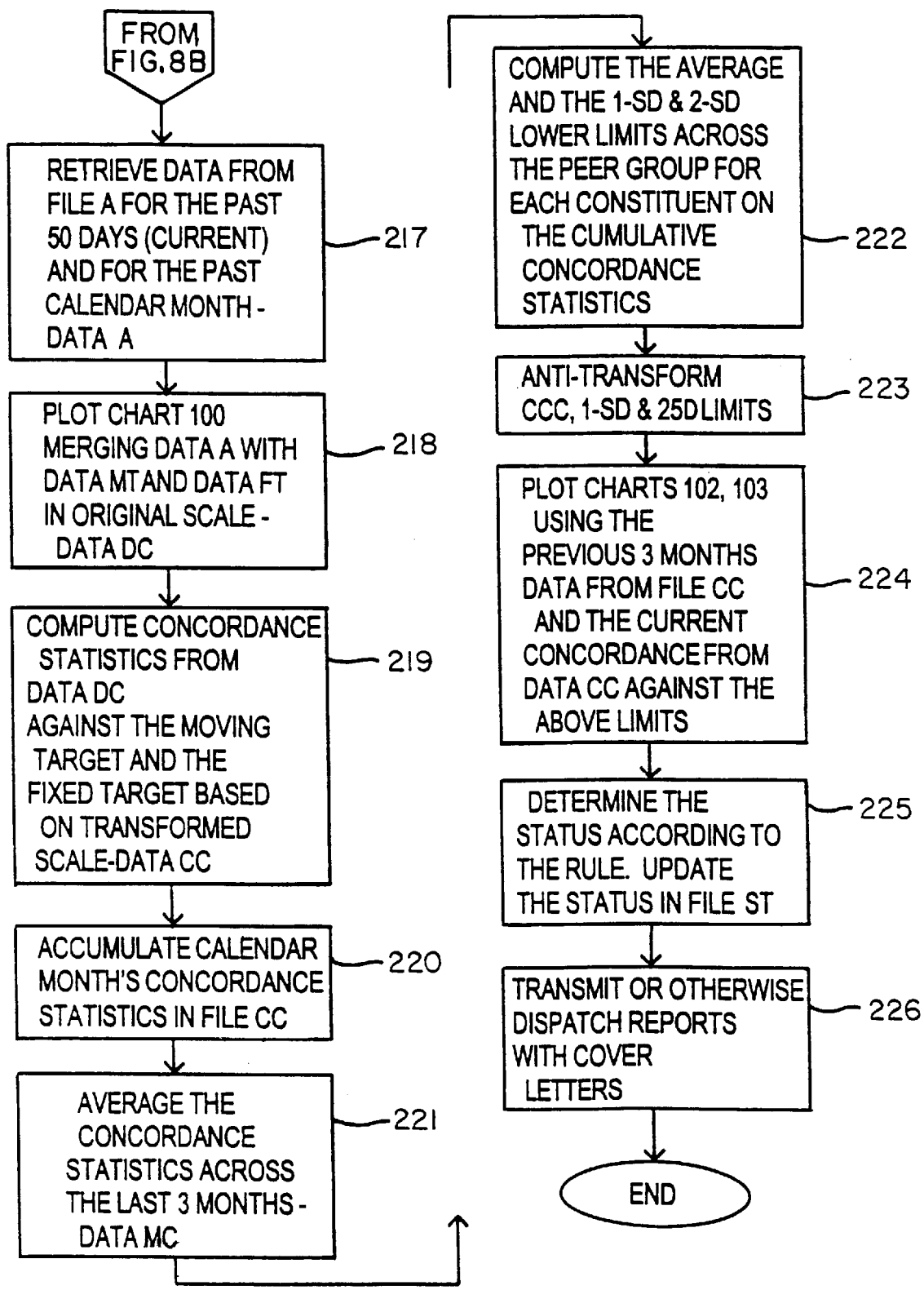

The operation of the system as well as its structure and functionality will be reviewed, but in the context of a flowchart (FIGS. 8A–8C) showing the process flow for information at the central station 40. It will be appreciated that the portions of the system which include the communication circuitry at the instruments, the communication links, and even the communication interface circuitry at the central station, is not shown. The flowchart begins with a step 200 (FIG. 8A) which broadly carries out the functions of the system in receiving and formatting data received from the instruments. A test 201 is performed to determine if valid control data has been received. If it has, the program branches to a step 202 which accumulates the control data in a file designated internally as File A. In the preferred practice of the invention, the only information accumulated in File A is the first set of control reading for each instrument for a given day. A step 203 is then performed to compute the weekly moving median for each control point for each instrument for the day in question, and store that information in File W. Step 204 accumulates the average of the WMM in a File C. The information collected in step 203 is that used for the moving target, whereas that accumulated in step 204 is utilized for the fixed target. A test 205 is then performed to determine if a report is to be generated. When no report is generated, and the process flow returns to the start. To satisfy a need for a report on demand (or real time reports), reports are preferably calculated on a very short interval of time (preferably daily) for the current window and the current month. Thus, in those situations, the test 205 will produce a positive result on a daily basis. As will be appreciated from the following, the CCC comparison and evaluation is performed on a daily basis, and can be reported to the laboratories on a daily basis, but historical statistics are typically stored on a monthly basis. This is facilitated in large measure by the rapid and automatic collection and processing of the information, such that ratings can be made and reports dispatched electronically within a day of receiving the control data, so that each instrument is continuously updated as to its status (by virtue of the current window on the report), while historical data of prior months is also kept and reported. In any event, when the test 205 generates a positive result, the subsequent process steps are performed to accumulate the statistics from the data already collected and prepare the necessary reports.

Before turning to those steps, it will be emphasized that the data which has been collected in the steps described thus far has all been collected automatically, without the need for any manual editing or manipulation. It will also be pointed out that the subsequent steps are also performed automatically and at electronic speed such that whenever a report is desired, or at the normal time of the month when a report is to be produced, the report can be produced promptly on data which had been collected up until that day, and distributed on the same day should that be desired.

Returning to FIG. 8, after the test 205 determines that a report should be generated, a first step is performed at 210 to compute and plot conventional summary statistics. The processing of this portion of the data output has not been described herein, because it is conventional. However, it is entirely possible using the information collection according to the invention to compute monthly, current and cumulative crude average, standard deviation and coefficient of variation statistics based on the raw data collected from all of the control measurements. While it is believed that such data is less useful than the concordance information to be described below, certain laboratories are accustomed to receiving it, and thus it can be provided as an added feature, if desired. However, since it has nothing to do with the practice of the present invention, further description will not be provided herein.

In practicing the invention, a step 211 is then performed to take the weekly moving median data from File W and merge it with the status information from File ST for the past 50 days (the current window) and for the past calendar month. A step 211 obtains the cumulative target information from File C and merges it with file ST. Thus, the result of steps 211 and 212 is to identify the control data for the instruments in the golden peer group for the dates in question (and for the cumulative), so that that information can be merged across instruments to determine moving and fixed targets. That operation is summarized in the step identified as 213. Step 214 is then performed to compute the golden peer group M-estimator average for each day to establish the daily moving target, and to store such information as data MT. The fixed target for the golden peer group is computed in step 215 and that data is stored as data FT. A step 216 updates the file FT with the new estimated fixed target value, and that new fixed target value is used in subsequent steps until again updated.

The process then proceeds to a step 217 which retrieves data from File A for the past 50 days (the current window) and for the past calendar month. That data is identified as Data A. It will be recalled that File A (and thus Data A) are the control data obtained from each of the laboratories to be rated. A step 218 is then performed to plot the chart 100 (FIG. 2) by merging Data A with the Data MT and Data FT (the moving and fixed targets) in the original scale. That data is also retained for further processing as Data DC. A step 219 is then performed to compute the concordance statistics from Data DC against the moving target and the fixed target based on the transformed scale. The computed concordance statistics for each instrument are stored as Data CC.

As noted above, the data is transformed according to transformations empirically determined for data distribution to accommodate skewed data sets. It is desirable in computing and comparing concordance correlation coefficients to have a normal bell-shaped curve, with the result being that for all readings within ±2 standard deviations from the average will encompass 95% of the observations. If the data set is skewed, that conclusion will not apply. As a result, for skewed data sets, it is typical to utilize data transformations, such as the power function, the logarithmic function, the hyperbolic tangent transformation, or the inverse hyperbolic tangent transformation, in order to produce data sets which contain the ordinary bell shape. The average and standard deviations are then computed for the transformed data, and then the average and one and two SD limits are antitransformed. Even as anti-transformed, they then encompass (within two SD's) 95% of the population.

Thus, the concordance statistics are determined based on the transformed data, and the nature of the transformation will be determined by the type of data set and a transformation empirically determined for the particular type of skew which it exhibits. It will be appreciated that the step 219 is performed both for the moving target data and also for the fixed target data, and thus each instrument being evaluated will have two concordance correlation coefficients for the month and two for the current 50-day window. The inverse hyperbolic tangent transformation is applied to the CCC data to achieve a Gaussian distribution, following which a step 220 accumulates the calendar month concordance statistics in a file CC (along with similar statistics accumulated in prior months). A step 221 then averages the concordance statistics across the last three months, with the average data being stored as Data MC. The average is performed for all instruments within the peer so as to produce an average value for the CCC for all instruments in the peer. A step 222 is then performed to compute the average and 1 SD and 2 SD lower limits across the peer group for each constituent. This distribution information is important in that it rates each instrument with respect to its peers. Furthermore, by virtue of the transformations, the population within the two SD limits is approximately 97.5% (one-sided) of the population, and thus the laboratory knows if it is performing within two SD's, it is at that level. Within one SD is typically classified as the good performing instruments which are eligible for entry into the golden peer group. Having computed the average CCC and the one and two SD limits, those CCC's and limits are then antitransformed in a step 223 (the inverse hyperbolic tangent antitransformation) to return to their original scale. This is the information which is plotted at 102 and 103 of the chart of FIG. 2. The actual plot is accomplished in the step 224, using the CCC information (average and SD limits) for the previous three months taken from File CC and also for the current concordance against the limits computed in step 223.

A step 225 is performed to determine the status of individual instruments within the peer. Those which have performed within one SD for three consecutive periods are rated as golden peers, and will be used as the golden peers in computation of the CCC for the next succeeding period. Having determined the final information in step 225, step 226 then transmits or otherwise dispatches the reports (such as FIG. 2) with the covering letters to the individual laboratories within the peer. Preferably, this is accomplished electronically on the communication channels 31 within one day or less of receiving the control data reports from the individual instruments.

The above description has focused on a single type of test reported from many sites, and the processing of the information relating to those tests, in order to rate all of the instruments with respect to their peers. What has not been focused on in any detail is the fact that the system according to the present invention is capable of and indeed is intended to perform that function for a large plurality of laboratory test instruments performing tests on numerous kinds of samples. Thus, there will be many peer data bases and control data data bases within the memory, and it will be necessary to operate on each independently, much as described above. However, when one fully appreciates the large number of laboratories and the varied kinds of data which are reported, one can appreciate that literally millions of data entries will be made per day in such a system. The ability of the system to automatically process the data without the need for human intervention or editing, coupled with the ability to automatically assign a single rating to a laboratory for a given period, coupled with the ability to then examine that rating with respect to the peers to determine a measure of quality, provides for a system which can process such large amounts of data effectively and in a timely fashion and at the same time produce results which are meaningful in validating the output on patient samples being regularly processed.

What is claimed is:

1. A method of reporting quality control ratings for instruments in a peer group of instruments performing the same analysis, in which the peer group of instruments periodically performs the analysis on known calibration samples to produce control readings which are reported to a central station for processing, the method comprising the steps of (a) determining and reporting for a given one of said instruments a concordance correlation coefficient CCC comprising a single number representative of accuracy and repeatability of the control readings for the given instrument compared against targets determined from a golden peer group selected as a subset of the best performing instruments in the peer group, and (b) weighting the concordance correlation co-efficient for the given station against the entire peer group by determining and reporting the value and distribution of CCC's for all instruments in peer group.

2. The method of claim 1 in which the step (a) is based on comparison of control readings for the given instrument and targets from the golden peer group performed on a periodic basis, and the step (a) determines and reports a single CCC for the given station based on comparisons for n periods where n is an integer greater than 1.

3. The method of claim 2 wherein the period is approximately daily, and n is selected to produce and store monthly reports.

4. The method of claim 3 wherein the step (a) of determining and reporting is performed daily and a "current" period is reported based on comparisons for the most recent m days.

5. The method of claim 3 wherein the steps of reporting reports both monthly comparisons and on comparisons for the last m days.

6. The method of claim 1 in which the step (a) of reporting also reports information on the correlation comparisons of the periodic control readings against the targets.

7. The method of claim 5 in which the step (a) of reporting also reports information on the correlation comparisons of the periodic control readings against the targets for the last m days.

8. In a system for storing and reporting quality control ratings for an instrument in a peer group of instruments performing the same test, and in which the instruments perform periodic tests on a control sample to produce control readings and report the control readings to a central station, the system including memory locations and a processor for determining and storing information comprising (a) periodic concordance comparisons of the control data for the given instrument against targets determined from a golden peer group selected from the best performing instruments in the peer group, (b) cumulative concordance ratings for n periods in which a concordance correlation coefficient CCC uses a single number to indicate accuracy and repeatability of the given instrument against the golden peer group targets over an interval of n periods, and (c) the value and statistical distribution of CCC's of all instruments in the peer group for the same interval of n periods.

9. The system of claim 8 in which the cumulative rates are based on comparison of control readings-for the given instrument and targets from the golden peer group performed on a periodic basis to report a single CCC for the given station based on comparisons for n periods, where n is an integer greater than 1.

10. The system of claim 9 wherein the period is approximately daily, and n is selected to produce and store monthly reports.

11. The system of claim 10 wherein the periodic concordance comparisons are performed daily and a "current" period is reported based on comparisons for the most recent m days.

12. The system of claim 11 wherein the memory stores information for both monthly comparisons and for comparisons for the last m days.

13. The system of claim 12 in which the memory stores information on the correlation comparisons of the periodic control readings against the targets for the last m days.

* * * * *